United States Patent [19]

Shirahata

[11] Patent Number: 4,814,474

[45] Date of Patent: Mar. 21, 1989

[54] METHOD FOR THE PRODUCTION OF TERTIARY-ALKYLDIMETHYLHALOSILANE

[75] Inventor: Akihiko Shirahata, Chiba, Japan

[73] Assignee: Toray Silicone Co., Ltd., Tokyo, Japan

[21] Appl. No.: 212,461

[22] Filed: Jun. 28, 1988

[30] Foreign Application Priority Data

Jul. 9, 1987 [JP] Japan .................................. 62-171700
Aug. 17, 1987 [JP] Japan .................................. 62-203857

[51] Int. Cl.$^4$ .............................................. C07F 7/08
[52] U.S. Cl. .................................................. 556/477
[58] Field of Search ........................................ 556/477

[56] References Cited

U.S. PATENT DOCUMENTS 2,496,419  2/1950  Sommer ........................... 556/477 X
2,802,852  8/1957  George ................................ 556/477

FOREIGN PATENT DOCUMENTS 60-222492  11/1985  Japan .................................... 556/477
60-237092  11/1985  Japan .................................... 556/477

OTHER PUBLICATIONS

Journal of Organic Chemistry, vol. 43, 3649 (1978).

Primary Examiner—Paul F. Shaver
Attorney, Agent, or Firm—Carl A. Yorimoto

[57] ABSTRACT

A method for the production of tertiary-alkyldimethylhalosilane with the following general structural formula

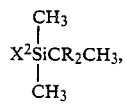

which comprises reacting a silicon compound having the general structural formula

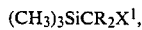

with a Lewis acid metal halide.

15 Claims, No Drawings

METHOD FOR THE PRODUCTION OF TERTIARY-ALKYLDIMETHYLHALOSILANE

BACKGROUND OF THE INVENTION

The instant invention relates to a method for the production of tertiary-alkyldimethylhalosilanes, which are useful as silylating agents and particularly as special silylating agents used for reaction control.

The following methods for the production of tertiary-alkyldimethylhalosilanes are known in the art. The reaction of a tertiary-alkyllithium reagent with dimethyldichlorosilane is described in *Journal of Organic Chemistry*, Volume 43, 3649 (1978) and *Journal of the American Chemical Society*, Volume 76, 1030 (1954).

A tertiary-alkyl Grignard reagent can be reacted with a halosilane having a relatively sterically unhindered Si-H group, for example, trihalosilane or methyldihalosilane, the residual halogen is converted to methyl by reaction with a methyl Grignard reagent, and the Si-H group is finally halogenated to afford the tertiary-alkyldimethylchlorosilane. This method is described in Japanese Patent Application Laid Open (Kokai) No. 60-22249(222,492/85).

Japanese Patent Application Laid Open No. 60-237092 (237,092/85) describes a method in which a disilane such as dimethyltetrahalodisilane or hexahalodisilane is reacted with a tertiary-alkyl Grignard reagent to prepare a tertiary-butylhalosilane, which is then partially methylate to produce the tertiary-alkyldimethylhalosilane.

SUMMARY OF THE INVENTION

The reaction of a tertiary-alkyllithium reagent with dimethyldihalosilane requires both the careful handling of highly active lithium metal as well as specialized equipment in order to prepare a highly active lithium microdispersion at elevated temperatures (approximately 200° C.). Moreover, this method is very dangerous because the obtained tertiary-alkyllithium spontaneously ignites merely upon contact with air.

The method of reacting a tertiary-alkyl Grignard reagent with a halosilane having a relatively sterically unhindered Si-H group entails a lengthy synthesis route. The reaction of a disilane with a tertiary-alkyl Grignard reagent, followed by partial methylation requires special disilanes and is inefficient because only half the silicon is utilized.

The object of the instant invention is to eliminate these problems by introducing a novel production method which affords tertiary-alkyldimethylhalosilane inexpensively, simply, and efficiently without the use of dangerous reagents. In the method of the instant invention for the production of tertiary-alkyldimethylhalosilane, because a silicon compound with the following general structural formula, $(CH_3)_3SiCR_2X^1$, is reacted with a Lewis acid metal halide, the target substance is produced in an inexpensive, simple, and efficient manner without the use of dangerous reagents. Because the tertiary-alkyldimethylhalosilane prepared by the instant invention's method of production contains a very bulky tertiary-alkyl substituent, it can be used as silylating agent in the synthesis of, for example, steroids, prostaglandins, etc.

DESCRIPTION OF THE INVENTION

In accordance with the instant invention, there is provided a method for the preparation of tertiary-alkyldimethylhalosilane under conditions that will be delineated herein. What is described, therefore, is a method for the production of tertiary-alkyldimethylhalosilane with the following general structural formula, $$\begin{array}{c} CH_3 \\ | \\ X^2SiCR_2CH_3, \\ | \\ CH_3 \end{array}$$

wherein each R in the formula is an alkyl group having 1 to 3 carbon atoms, wherein $X^2$ is a chlorine atoms or a bromine atom, said method comprising reacting a silicon compound having the general structural formula, $(CH_3)_3SiCR_2X^1$, wherein each R is an alkyl group having 1 to 3 carbon atoms and $X^1$ is a chlorine atom or bromine atom, with a Lewis acid metal halide selected from a group consisting of Lewis acid metal chlorides and Lewis acid metal bromides.

The silicon compound with the general formula, $(CH_3)_3SiCR_2X^1$, is a starting material in the instant invention's method of production. R in the above formula is an alkyl group having one to three carbon atoms, and this encompasses methyl, ethyl, and propyl. $X^1$ is a chlorine atom or a bromine atom. $X^1$ and $X^2$ can be the same or can be different. Such silicon compounds are readily prepared by reacting a Grignard reagent with the general formula, $R_2HCMgX^1$, (R and $X^1$ in the formula is defined as above) with trimethylchlorosilane to synthesize $(CH_3)_3SiCHR_2$ (R in the formula is defined as above), which is then reacted with chlorine or bromine under photoirradiation.

The Lewis acid metal chloride or Lewis acid bromide is used in the instant invention's metod of production both as a starting material and as a catalyst. The Lewis acid chloride can be, for example, aluminum chloride, ferric chloride, titanium tetrachloride, antimony chloride, and tin chloride. The Lewis acid bromide can be, for example, aluminum bromide, ferric bromide, titanium bromide, antimony bromide, and tin bromide. Aluminum chloride and aluminum bromide are preferred from the standpoints of reaction selectivity and reaction rate.

With regard to the quantity of use of this component, when $X^1$ is the chlorine atom in the silicon compound with the general structural formula, $(CH_3)_3SiCR_2X^1$, and $X^2$ is chlorine in the target silicon compound with the general structural formula,

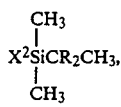

the Lewis acid metal chloride or Lewis acid metal bromide is used preferably at 0.01 to 10 mole% and more preferably at 0.1 to 2 mole% relative to the starting silicon compound. When $X^1$ in the starting silicon compound is the bromide atom and $X^2$ in the target silicon compound is the chlorine atom, the Lewis acid metal chloride will be used in a quantity providing preferably at least equimolar and more preferably 1 to 5 moles chlorine atoms therein per 1 mole of the starting silicon compound.

Furthermore, when $X^1$ in the starting silicon compound is the bromine atom and $X^2$ in the target silicon compound is also the bromine atom, Lewis acid metal chloride or Lewis acid metal bromide is preferably added at 0.01 to 10 mole% and more preferably at 0.1 to 2 mole% relative to the starting silicon compound.

No specific restriction is placed on the reaction atmosphere in the instant invention's method of production, and the reaction may be run in air or under an inert gas, at ambient, elevated, or reduced pressure.

The reaction may also be carried out in the presence of an organic solvent. Organic solvents can be, for example, brominated hydrocarbons such as methylene bromide; chlorinated hydrocarbons such as methylene chloride, chloroform, and carbon tetrachloride; and aromatic hydrocarbon solvents such as toluene and xylene. The use of organic solvent is preferred from the standpoints of controlling the reaction rate and contacting of reactants. The use of halogenated hydrocarbon solvents is even more preferred.

Furthermore, given the circumstances in which a chlorinated hydrocarbon solvent is used as the reaction solvent and $X^2$ in the target silicon compound is the chlorine atom and $X_1$ in the starting silicon compound is the bromine atom, and when the quantity of chlorine atoms in said solvent is at least equimolar with the starting silicon compound having the general formula,

the addition of Lewis acid metal chloride or Lewis acid metal bromide can then be as low as 0.01 mole% relative to the silicon compound because the chlorine atoms in the solvent participate in the reaction.

The reaction temperature is preferably 10° to 150° C. and more preferably 20° to 120° C.

So those skilled in the art may better understand and appreciate the instant invention, the following examples are presented. These examples are presented to be illustrative and are not to be construed as limiting the instant invention as claimed herein.

EXAMPLE 1

A solution of 150.7 g (1 mole) alpha-chloro-alphamethylethyltrimethylsilane and 100 g methylene chloride was slowly dripped into a suspension prepared from 100 g methylene chloride and 0.5 g (3.75 mmole) aluminum chloride. A methylene chloride reflux was established due to the exothermic reaction.

After the completion of addition, the reaction was brought to completion by heating the methylene chloride under reflux at 42° C. for an additional 1 hour with stirring. The reaction solution was filtered and then distilled at ambient pressure to remove the methylene chloride. Continuing distillation at ambient pressure afforded tertiary-butyldimethylchlorosilane (147 g, 0.0975 mole, yield=97.5%, bp=124° to 126° C.).

EXAMPLE 2

A solution of 195 g (2 mole) alpha-bromo-alpha-methylethyltrimethylsilane and 200 g methylene chloride was gradually dripped into a suspension prepared from 200 g methylene chloride and 0.5 g (3.75 mmole) aluminum chloride. A methylene chloride reflux was established due to the exothermic reaction.

After the completion of addition, the reaction was brought to completion by stirring at 42° C. for an additional 3 hours. The reaction solution was then filtered in order to remove the aluminum bromide. The methylene chloride and bromochloromethane (produced in the reaction) were then evaporated off, and the residue was directly distilled at ambient pressure to afford the tertiary-butyldimethylchlorosilane target (142 g, 0.94 mole, yield=94%, bp 124° to 126° C.).

EXAMPLE 3

A solution of 195 g (1 mole) alpha-bromo-alpha-methylethyltrimethylsilane and 200 g methylene bromide was slowly dripped into a suspension prepared from 50 g (0.375 mole) aluminum chloride and 200 g methylene bromide. A methylene bromide reflux was established due to the exothermic reaction.

After the completion of addition, the reaction was brought to completion by stirring at 100° C. for 30 minutes. The reaction solution was filtered to remove the aluminum bromide, the methylene bromide was evaporated off, and this was then directly distilled at ambient pressure to afford the tertiary-butyldimethylchlorosilane target (140 g, 0.93 mole, yield=93%, bp=124° to 126° C.).

EXAMPLE 4

A solution of 195 g (1 mole) alpha-bromo-alpha-methylethyltrimethylsilane dissolved in 200 g methylene bromide was slowly dripped into a suspension of 2.0 g (7.6 mmole) aluminum bromide in 200 g methylene bromide. A methylene bromide reflux was established due to the exothermic reaction. After the completion of addition, the reaction was brought to completion by stirring for an additional 1 hour with heating. The reaction solution was distilled at the ambient pressure to remove the methylene bromide, and distillation was continued at the ambient pressure in order to collect the fraction at 143° to 144° C. 192 grams of the tertiary-butyldimethylbromosilane target material was thus obtained at 98% yield.

EXAMPLE 5

While exposed to 100 W white light, 61.5 g (0.385 mole) bromine was dripped at 20° C. into a solution of 44.8 g (0.385 mole) trimethylisopropylsilane dissolved in 50 g dibromotetrafluoroethane. After the completion of addition, the solvent was heated under reflux in order to remove the hydrogen bromide and afford alpha-bromo-alpha-methylethyltrimethylsilane. Into this was then slowly dripped a solution of 1.0 g aluminum bromide in 10 g dibromotetrafluoroethane. After the completion of addition, the reaction solution was distilled at the ambient pressure to remove the solvent, and this distillation was continued in order to collect a fraction at 143° to 144° C. 67.6 g tertiary-butyldimethylbromosilane (yield=90%) was produced. This target substance was identified on the basis of the following spectral data.

NMR: delta (ppm): 0.45, singlet, 6H; 0.96, singlet, 9H.

MS: m/e (spectral intensity ratio), 70 eV: 196 (8.1), 194 (7.9), 139 (80.1), 137 (79.8), 111 (5.0), 109 (10.5), 107 (6.0), 73 (17.5), 57 (69.4), 56 (100).

What is claimed is:

1. A method for the production of tertiary-alkyldimethylhalosilane with the following general structural formula, $$\begin{array}{c} CH_3 \\ | \\ X^2SiCR_2CH_3, \\ | \\ CH_3 \end{array}$$

wherein each R in the formula is an alkyl group having 1 to 3 carbon atoms, wherein $X^2$ is a chlorine atom or a bromine atom, said method comprising reacting a silicon compound having the general structural formula, $$(CH_3)_3SiCR_2X^1,$$

wherein each R is an alkyl group having 1 to 3 carbon atoms and $X^1$ is a chlorine atom or bromine atom, with a Lewis acid metal halide selected from a group consisting of Lewis acid metal chlorides and Lewis acid metal bromides.

2. A method, according to claim 1, wherein the Lewis acid metal halide is selected from a group consisting of aluminum chloride and aluminum bromide.

3. A method, according to claim 1, wherein the tertiary-alkyldimethylhalosilane has the general structural formula, $$\begin{array}{c} CH_3 \\ | \\ ClSiCR_2CH_3, \\ | \\ CH_3 \end{array}$$

4. A method according to claim 3, wherein the silicon compound has the general structural formula, $$(CH_3)_3SiCR_2Cl;$$

and the Lewis acid metal halide is present at a concentration in a range from about 0.01 to 10 mole percent relative to the silicon compound.

5. A method according to claim 4, wherein the Lewis acid metal halide is present at a concentration in a range from about 0.1 to 2 mole percent relative to the silicon compound.

6. A method according to claim 3, wherein the silicon compound has the general structural formula, $$(CH_3)_3SiCR_2Br;$$

and the Lewis acid halide is a Lewis acid metal chloride and is present at a concentration equal to or greater than about 1 mole chlorine atom per mole of silicon compound.

7. A method according to claim 6, wherein the Lewis acid metal chloride is present at a concentration in a range from about 1 to 5 moles chlorine atoms per mole of silicon compound.

8. A method, according to claim 1, wherein the tertiary-alkyldimethylhalosilane has the general structural formula, $$\begin{array}{c} CH_3 \\ | \\ BrSiCR_2CH_3; \\ | \\ CH_3 \end{array}$$

the silicon compound has the general structural formula $$(CH_3)_3SiCR_2Br;$$

and the Lewis acid metal halide is present at a concentration in a range from about 0.01 to 10 mole percent relative to the silicon compound.

9. A method according to claim 8, wherein the Lewis acid metal halide is present at a concentration in a range from about 0.1 to 2 mole percent relative to the silicon compound.

10. A method according to claim 1, wherein the reaction of the silicon compound with a Lewis metal halide is carried out in the presence of an organic solvent.

11. A method according to claim 10, wherein the organic solvent is selected from a group consisting of halogenated hydrocarbons, chlorinated hydrocarbons, and aromatic hydrocarbons.

12. A method according to claim 6, wherein there is present a chlorinated hydrocarbon, said chlorinated hydrocarbon being present such that the concentration of chlorine atoms in the solvent are greater on a molar basis than the concentration of the silicon compound, and the Lewis acid metal chloride is present at a concentration equal to or greater than about 0.01 mole percent relative to the silicon compound.

13. A method according to claim 1, wherein te reaction is carried out at a temperature in a range from about 10° to 150° C.

14. A method according to claim 1, wherein the tertiary-alkyldimethylhalosilane is tertiary-butyldimethylchlorosilane.

15. A method according to claim 1, wherein the tertiary-alkyldimethylhalosilane is tertiary-butyldimethylbromosilane.

* * * * *